United States Patent [19]
Cane et al.

[11] Patent Number: 5,762,605
[45] Date of Patent: Jun. 9, 1998

[54] ERGONOMIC HAND-HELD OPTICAL DIAGNOSTIC INSTRUMENT

[76] Inventors: Richard M. Cane; Wayne R. Byard, both of 13790 NW. 4th St., Sunrise, Fla. 33325

[21] Appl. No.: 565,176

[22] Filed: Nov. 30, 1995

Related U.S. Application Data

[63] Continuation-in-part of Ser. No. 107,889, Aug. 19, 1993, abandoned, which is a continuation-in-part of Ser. No. 797,724, Nov. 25, 1991, Pat. No. 5,239,984.

[51] Int. Cl.⁶ .............................. A61B 1/04; A61B 1/227
[52] U.S. Cl. ........................ 600/200; 600/131; 600/112
[58] Field of Search ............................. 600/109, 112, 600/131, 170, 175, 200, 188; 433/29, 30, 31; 348/65

[56] References Cited

U.S. PATENT DOCUMENTS

| | | | |
|---|---|---|---|
| 3,373,737 | 3/1968 | Moore et al. | 600/200 |
| 4,331,132 | 5/1982 | Mukasa | 600/117 |
| 4,413,278 | 11/1983 | Feinbloom | 600/112 |
| 4,565,423 | 1/1986 | Ueda | 600/112 |
| 4,905,082 | 2/1990 | Nishigaki et al. | 600/109 |
| 5,217,003 | 6/1993 | Wilk | 600/109 |

*Primary Examiner*—Richard J. Apley
*Assistant Examiner*—John Leubecker
*Attorney, Agent, or Firm*—Melvin K. Silverman

[57] ABSTRACT

An optical diagnostic system for use within a convention physician-patient examining distance, not exceeding the manual reach of the doctor, including an ergonomic, hand-held, non-surgical, optical diagnostic medical instrument having a light image input-to-output pathway corresponding to an axis of examination, the instrument including an integral gripping assembly for gripping by the physician, and the instrument also including a light source from the pathway and power supply, a light-tight optical coupling for re-directing light received from the light pathway along the axis of examination to a pathway substantially normal thereto, that pathway defining an axis of manipulation and, in optical communication with the coupling, a micro-video camera for generating an electronic signal corresponding to the re-directed light image from the coupling, the micro-video camera including an exterior housing defining, in combination with the gripping assembly of the medical instrument, an axis of manipulation substantially co-linear with the pathway of re-directed light from the optical coupling. Therein the examining physician may grip both the instrument handle and the micro-video camera housing within the same hand to define the axis of manipulation, and, thereby to establish the axis of examination in a manner which is ergonomically advantageous to both the physician and patient.

6 Claims, 3 Drawing Sheets

ERGONOMIC HAND-HELD OPTICAL DIAGNOSTIC INSTRUMENT

REFERENCE TO RELATED APPLICATION

This case is a continuation-in-part of application Ser. No. 08/107,889, filed Aug. 19, 1993, entitled Hand-held Opto-diagnostic Instrument System, now abandoned, which is a continuation-in-part of application Ser. No. 07/797,724, filed Nov. 25, 1991, entitled Hand-Held Opto Diagnostic Instrument System, now U.S. Pat. No. 5,239,984.

BACKGROUND OF THE INVENTION

Various hand-held instruments for use by a physician during office examination of a patient have been known in the art for many years. Such hand-held instruments include the otoscope (for examination of the ear), ophthalmoscope (for examination of the eye), larynx illuminator (throat), nasopharynx illuminator (nasal passages), dermatologic magnifier (skin) and anoscope (lower G.I. tract).

Also, in the prior art, it has been known to employ miniature or micro-video cameras in connection with various surgical procedures which occur in the operating room. One example of such prior art is U.S. Pat. No. 4,963,903 (1990) entitled Camera Positioning System, to Richard M. Cane, one of the within co-inventors. Such video cameras are, technically, known as remote head color CCD cameras. Such cameras employ an array of semi-conductive chips using a technology known as charge coupled diode sensors. Such micro-cameras are capable of yielding more than 500 lines of resolution per axis, resulting from the use of 400,000 or more pixels on the screen. Use of such micro-video cameras and related equipment, such as endocouplers, have been known for some time in connection with certain types of surgery and, particularly, surgery conducted through the use of small incisions in the body wall in videoendoscopy procedures. Such procedures have become increasingly commonplace in connection with procedures upon the gall bladder, appendix, intestine, and reproductive organs where the problem is of an internal nature.

Despite the relatively widespread use of micro-video technology in the operating room, which includes the display of a procedure upon both local and remote monitors, the benefits of this technology have not manifested themselves in the physician's office within the context of otherwise routine examination and diagnosis.

The need for, and benefit of, the expression of this technology into an office examination environment has become evident in many areas. In the first instance, the patient and doctor could both observe, upon a local monitor, a greatly enlarged image of the examination. A video record of such examination might be kept, and the patient and doctor, or provided with either the video of selected positive print frames of a video tape of the examination.

Enhanced light may be furnished to the site of observation, and extra battery power or A/C power may be provided at the doctor's hand held instrument. Also, in a more exotic context, a video link to a satellite or other transmission means may be provided from a video interface of the system such that consultants may be utilized either in real time, or in a batch mode, to provide "second opinions" to the examining physician or paramedic who may be located in a geographically remote region and/or may possess limited skills in the specialty to which the examination relates. Such activity has become known as telemedicine.

Moreover, many of the optical instruments present in the art are awkward in use, as those instruments are difficult for the examining physician to hold, manipulate and easily obtain the necessary views for the examination without causing the patient to rest in an awkward position or causing the physician to contort his holding of the instrument. This is primarily due to fact that the optical instruments common in the art are designed to accommodate their electronic components, rather than the ergonomics of the physician's hand and the necessary positions for examining the patient.

The instant invention may thereby be understood as an ergonomic enhancement of the power and utility of conventional hand-held, in-office medical diagnostic instruments in the nature of the otoscope, ophthalmoscope, larynx illuminator and nasopharynx illuminator, dermatologic magnifier and anoscope.

Examples of prior art optical examination systems which do no include such ergonomic enhancement are U.S. Pat. No. 4,590,923 to Watanable, entitled Arthroscope Video Camera Assembly and U.S. Pat. No. 4,905,802 to Nishigaki, et al, entitled Video Endoscope with Detachable Imaging Unit.

SUMMARY OF THE INVENTION

The instant invention relates to an optical diagnostic system for use within a conventional physician-patient examining distance, not exceeding the manual reach of the doctor, including an ergonomic, hand-held, non-surgical, optical diagnostic medical instrument having a light image input-to-output pathway corresponding to an axis of examination, the instrument including an integral gripping assembly for gripping by the physician, and the instrument also including a light source from the pathway and power supply, a light-tight optical coupling for re-directing light received from the light pathway along the axis of examination to a pathway substantially normal thereto, that pathway defining an axis of manipulation and, in optical communication with the coupling, a micro-video camera for generating an electronic signal corresponding to the re-directed light image from the coupling, the micro-video camera including an exterior housing defining, in combination with the gripping assembly of the medical instrument, an axis of manipulation substantially co-linear with the pathway of re-directed light from the optical coupling. Therein the examining physician may grip both the instrument handle and the micro-video camera housing within the same hand to define the axis of manipulation and, thereby, to establish the axis of examination in a manner which is ergonomically advantageous to both the physician and patient.

The ergonomic hand-held instrument may take a variety of forms including, without limitation, an otoscope, an ophthalmoscope, larynx and nasopharynx illuminators, dermatologic magnifiers and anoscope.

It is, accordingly, an object of the present invention to provide a means for observing, in real time, by both doctor and patient, an enlarged image of the subject of a physician's examination with an ergonomic hand-held optical diagnostic instrument.

It is another object to provide a means for storage and later review of the medical subject of the examination by said ergonomic hand-held optical diagnostic instrument.

It is a further object of the present invention to provide a means by which the object of such examination may be electronically linked to other physicians, i.e., telemedicine.

It is a yet a further object to provide a system of the above type to furnish to the examining doctor enhanced illumination, extended battery capability, manipulability through ergonomic design, and the means to explain, both concurrently with and following the examination, his findings to the patient and other parties.

The above and yet other objects and advantages of the invention will become apparent from the hereinafter set forth Brief Description of the Drawings, Detailed Description of the Invention, and claims appended herewith.

DETAILED DESCRIPTION OF THE INVENTION

Figure 1:
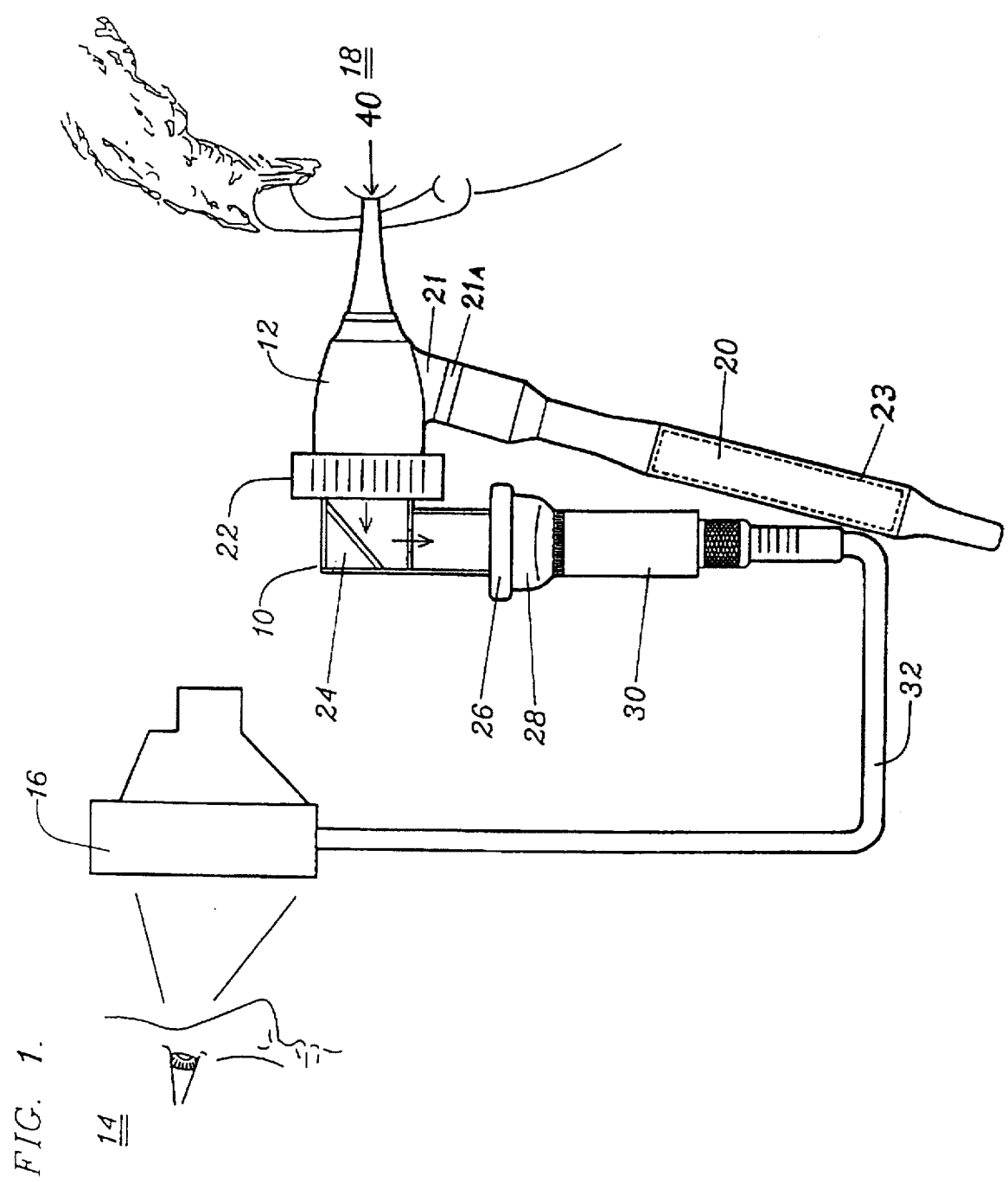
FIG. 1 is a conceptual view showing usage by a physician of an otoscope embodiment of the instant invention.

The instant inventive system provides for the placement of an optical coupler 10 in light-tight relationship about a light image input-to-output pathway of an ergonomic optical diagnostic instrument 12 such as the otoscope shown in FIG. 1 for the viewing of a diagnostic image 40 of patient 18.

Figure 1A:
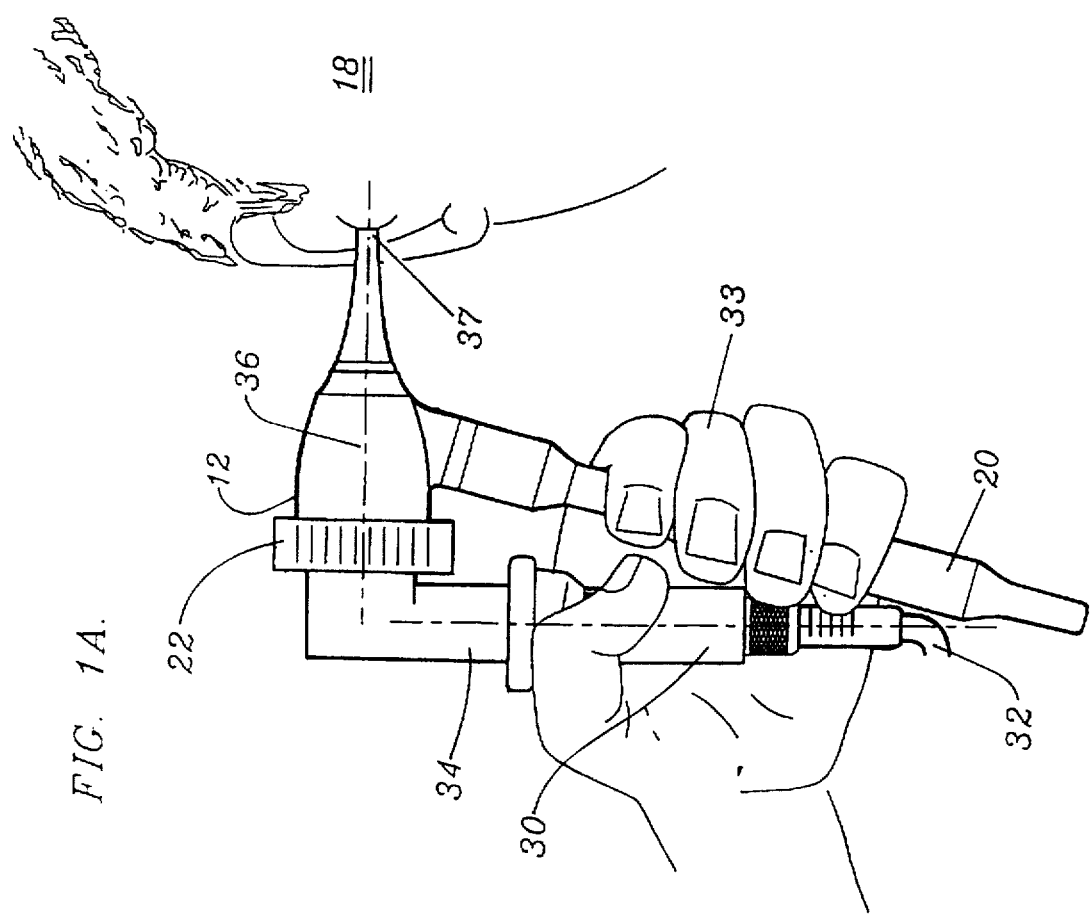
FIG. 1A is an operational view showing the position of the hand of the physician relative to the axis of manipulation.

With reference to FIG. 1A there is shown the manner in which said handle 20 and the external housing of the micro-video camera 30 are engaged by a hand 33 of the examining physician 14. As may be noted, the physician is able to define an axis of manipulation 34 which thereby operates to define an axis of examination 36. Said axis 36 begins at an optical input 37, also known as the speculum of the examining instrument, which is inserted into the audio (ear) or nasal passageway of the patient 18. The diameter of said input 37 will be in the range of about one-quarter to about one-half inch.

Also shown in the view of FIG. 1A is a video image path which provides to the physician a view along the axis 36 of examination utilizing the video monitor 16 in the manner shown in FIG. 1. In any event, the physician, through the ability to define the axis of manipulation and, thereby, the axis of examination without need to reposition cable 32 or other cables, is provided with a system that is highly ergonomic with respect to the needs of both the physician and the patient. As may be appreciated, the housing of the micro-video camera is proportioned to the hand 3 of the physician as is the handle 20 of the instrument 12 such that a virtual circumference about said housing of the micro-video camera and said handle 20 of the diagnostic instrument is proportioned for engagement by the hand 3 of the physician, that is by the hand of an adult human. It is thereby to be appreciated that the cross-section of the housing of the micro-video camera and the cross-section of the gripping means of the diagnostic instrument are generally proportioned in physical size to each other in order to facilitate concurrent engagement of both by the hand of the physician to define a means of manipulation for the diagnostic instrument, that is, a means of permitting the examining physician to grip both the instrument handle and the housing of said micro-video camera with the same hand to define said means for manipulation of the diagnostic instrument in a manner which is ergonomicaly advantageous to both physician and patient. 12. There is thereby provided an integrated examining and video recording system that does not in any fashion interfere with the traditional manner of physician usage of opto-diagnostic endoscopes, such as otoscope, nasal illuminators, and larynx illuminators, dermatologic magnifiers and anoscopes.

It is noted that handle 20 will typically include a light source 21 such as a bulb and a power source 23 therefore, such as a battery or AC input. Handle 20 may also include an alternative light source 21a optically coupled to said instrument 12.

With further reference to FIG. 1, it may be seen that optical coupler 10 includes an adapter 22 which operates to integrate coupler 10 about the eyepiece or input-to-output pathway of the ergonomic hand-held instrument 12.

Further, in FIG. 1, it may be seen that the light image (indicated by the arrows within optical coupler 10) enters the coupler from the instrument 12, reflects off of mirror 24 and is re-directed normally and downwardly through micro-camera lens clamp 26, through micro-camera C-mount adaptor 28 and micro-camera head 30. Therefrom, the received light image passes through electrical cable 32 to said video monitor 16.

Figure 4:
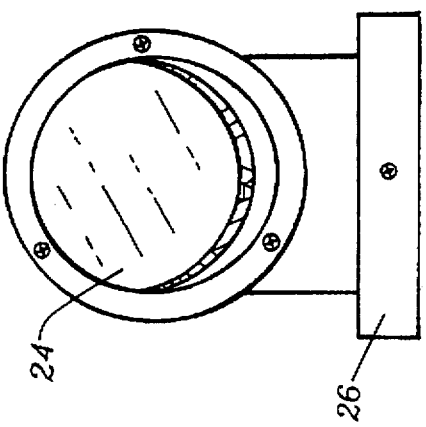
FIG. 4 is a front view of the optical coupler shown in FIG. 3.
Figure 3:
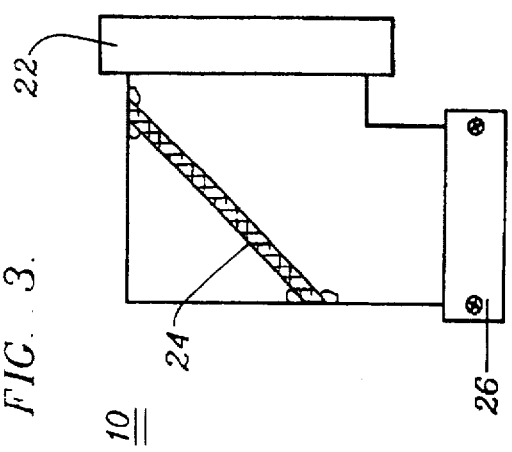
FIG. 3 is a side cross-sectional view of the optical coupling of the instant invention.

The interior structure of the optical coupler 10, including said adapter 22, mirror 24, and clamp 26, is more particularly illustrated in the side and front enlarged views of FIG. 3 and FIG. 4.

Figure 2:
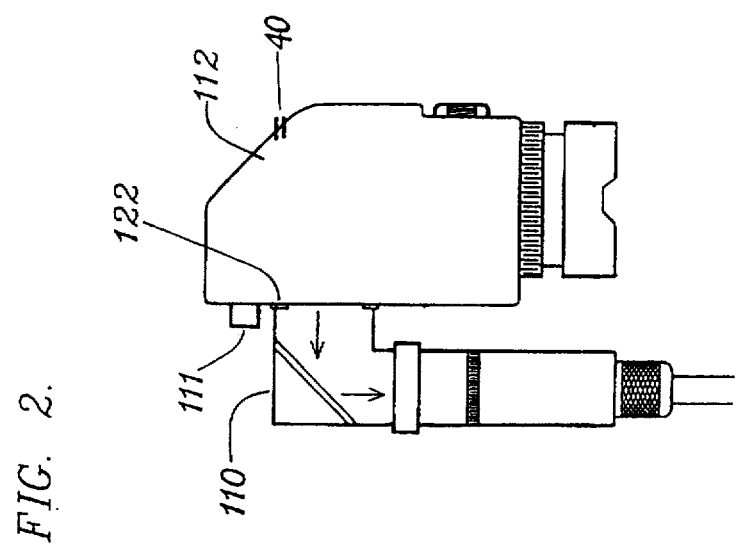
FIG. 2 is a conceptual view showing an ophthalmoscope embodiment of the invention.

With reference to the view of FIG. 2, there is shown an ophthalmoscope embodiment of the invention which, in all respects, follows the above-described operation of the system in FIG. 1. In the embodiment of FIG. 2, optical coupler 110 is integrated into ophthalmoscope 112 such that the physician 14 may observe (see light input image 40) the eye of the patient upon monitor 16, in lieu of the much smaller image that would normally be available through the eyepiece 111 of the ophthalmoscope. The shape of adapter 122 will, in the embodiment of FIG. 2, differ from that of adapter 22 of FIG. 1.

Figure 5:
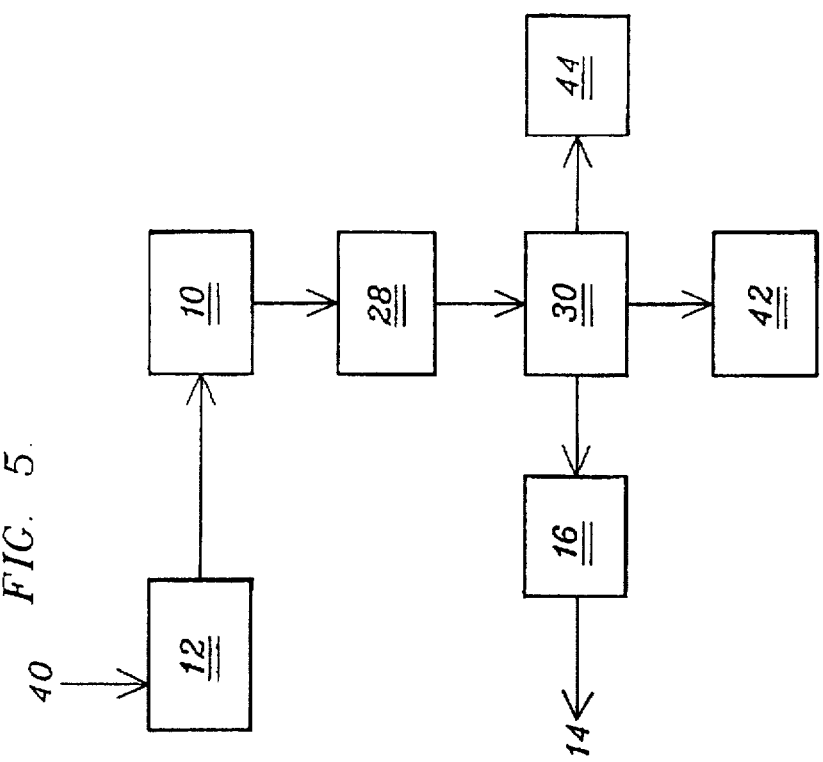
FIG. 5 is a block diagrammatic view of the inventive system including optical components therefore.

With reference to the block diagram view of FIG. 5, the basic flow of optical information may be seen to originate said diagnostic image 40 which passes through the optical pathway within the ergonomic hand-held optical diagnostic instrument 12 and, therefrom, into optical coupler 10, which, as is noted, may comprise said mirror 24, a prism, or any other coupling capable of bending light. It is further noted that in the case of certain opto-diagnostic instruments, it will not be necessary to cause the light of image 40 to circumvent a right angle, as is shown in FIG. 1 and FIG. 2. In such instruments, the optical pathway will simply be a straight one between the image input 40 and the micro-camera head 30.

With further reference to FIG. 5 the optical information exits optical coupler 10, passes through micro-camera lens 28 to camera head 30 and, finally, to video monitor 16 at which it is observed by doctor 14. Shown as peripheral attachments to camera 30 are printer 42 and communications link 44. Through such a communications link, examination may be effected by a non-doctor, such as a nurse or paramedic in a non-hospital environment, while information is transmitted via satellite or otherwise to a doctor at a remote location, such that the on site paramedic can be provided with real time suggestions for treatment of the patient 18 (i.e., telemedicine).

Accordingly, while there has been shown and described a preferred embodiment of the present invention, it is to be appreciated that the invention may be embodied otherwise than is herein specially shown and described and, within such embodiments, certain changes may be made in the form and arrangement of the parts without departing from the underlying ideas and principles of this invention within the scope of the Claims appended herewith.

Having thus described our invention what we claim as new, useful and non-obvious and, accordingly, secure by Letters Patent of the United States is:

1. An optical diagnostic system for use within a conventional physician-to-patient examining distance not exceeding the manual reach of a physican, the system comprising:

(a) an ergonomic hand-held, non-surgical optical diagnostic medical instrument having a light image input-to-output pathway defining an axis of examination of the patient, said instrument further including integral gripping means for gripping by the physician, said instrument also including a light source for said pathway and a power supply therefor;

(b) an optical coupling for re-directing light received from said light image pathway along said axis of examination to a pathway substantially normal thereto, said coupling in optical communication with said light image pathway; and (c) in optical communication with said coupling, a micro-video camera generating an electronic signal corresponding to re-directed light from said coupling, said micro-video camera including an exterior housing proximal to said gripping means defining, in combination with said gripping means of said instrument, means for manipulation of said instrument, said manipulation means disposed substantially co-linearly with said pathway of said re-directed light from said optical coupling, said micro-video camera proportioned in radial cross-section to about the radial cross-section of said gripping means of said diagnostic instrument, in which a virtual circumference, about both of the external housing of said micro-video camera and said gripping means of said instrument, is proportioned for engagement by the hand of an adult human.

2. The system as recited in claim 1 in which said system further comprises:

a video monitor and recording means coupled to an output of said micro-video camera, said video monitoring and recording means adapted to be situated within a line-of-sight proximal to the physician during patient examination.

3. The system as recited in claim 2, in which said medical instrument comprises:

a housing operably connected to said gripping means in the range of about one-quarter inch to about one-half inch in diameter.

4. The system as recited in claim 3, in which said optical coupling comprises:

means for altering the directionality of said light received from said input-to-output pathway.

5. The system as recited in claim 2, further comprising:

an informational transmissional link electronically connected to an output of said micro-video camera.

6. The system as recited in claim 1, further comprising:

a supplemental non-battery power source for said light source.

* * * * *